(12) United States Patent
Boyd et al.

(10) Patent No.: US 8,475,414 B2
(45) Date of Patent: Jul. 2, 2013

(54) MEDICATION DELIVERY DEVICE AND METHOD FOR OPERATING A MEDICATION DELIVERY DEVICE

(75) Inventors: Malcolm Boyd, Leamington (GB); Robert Veasey, Warwickshire (GB); David Plumptre, Worcestershire (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 767 days.

(21) Appl. No.: 12/326,133

(22) Filed: Dec. 2, 2008

(65) Prior Publication Data

US 2010/0137792 A1 Jun. 3, 2010

(51) Int. Cl.
*A61M 5/315* (2006.01)
(52) U.S. Cl.
USPC .......................... 604/218; 604/220; 604/225
(58) Field of Classification Search
USPC ............... 604/68, 69, 70, 71, 72; 605/68, 69, 605/70, 36, 71, 72, 131, 133, 134, 135, 186, 605/207, 208, 209, 210, 211, 218, 220, 225, 605/228, 229, 232, 233, 234, 235, 246, 230
See application file for complete search history.

(56) References Cited

U.S. PATENT DOCUMENTS 7,517,334 B2 * 4/2009 Jacobs et al. .................. 604/110
7,678,084 B2 * 3/2010 Judson et al. ................. 604/187

* cited by examiner

*Primary Examiner* — Laura Bouchelle
*Assistant Examiner* — Brooke Matney
(74) *Attorney, Agent, or Firm* — McDonnell Boehnen Hulbert & Berghoff LLP

(57) ABSTRACT

A medication delivery device (1) comprises a housing (4) having a proximal end (P) and a distal end (D), a cartridge (3) for holding a medication (M), the cartridge (3) having an outlet (2), a moveable piston (5) being retained within the cartridge (3), a drive member (17) moveable in a proximal direction with respect to the housing (4) for setting a dose of medication (M) to be delivered and in the distal direction with respect to the housing (4) for delivering the dose and a piston rod (10) adapted to drive the piston (5) in a distal direction with respect to the cartridge (3) for delivering the dose. The drive member (17) is releasably coupled to the piston rod (10). The medication delivery device (1) further comprises a resilient member (21) which is arranged to move the drive member (17) in the proximal direction with respect to the housing (4) after dose delivery, thereby reducing pressure of the piston rod (10) on the piston (5).

24 Claims, 7 Drawing Sheets

MEDICATION DELIVERY DEVICE AND METHOD FOR OPERATING A MEDICATION DELIVERY DEVICE

The present invention relates to a medication delivery device for the administration of a dose of a drug, for example insulin or heparin. The medication delivery device may be a pen-type injector to administer a number of pre-set doses of a medication. In particular, the device may be a device where a user may activate the medication delivery device.

Such medication delivery devices may have application where persons without formal medical training, i.e. patients, need to administer an accurate and predefined dose of a medication. In particular, such devices may have application where medication is administered on a regular or an irregular basis over a short-term or long-term period.

WO 02/05876 A2 discloses a liquid medication delivery device for delivering an intended dose, the device comprising an engine.

U.S. Pat. No. 4,601,212 discloses a precision micropipettor device, which includes a spring for returning a plunger shaft assembly to a preferred resting position after each use.

The object of the invention is to provide a medication delivery device and a method for operating the medication delivery device which enable a simple and precise usage of the medication delivery device. In particular, it is an aim to reduce weeping of medication from the medication delivery device after dose delivery.

The object is achieved by the features of the independent claims. Advantageous embodiments are given in the subclaims.

BRIEF DESCRIPTION OF THE DRAWINGS

Elements of the same design and function that are shown in different illustrations are identified by the same reference numeral.

Figure 1:
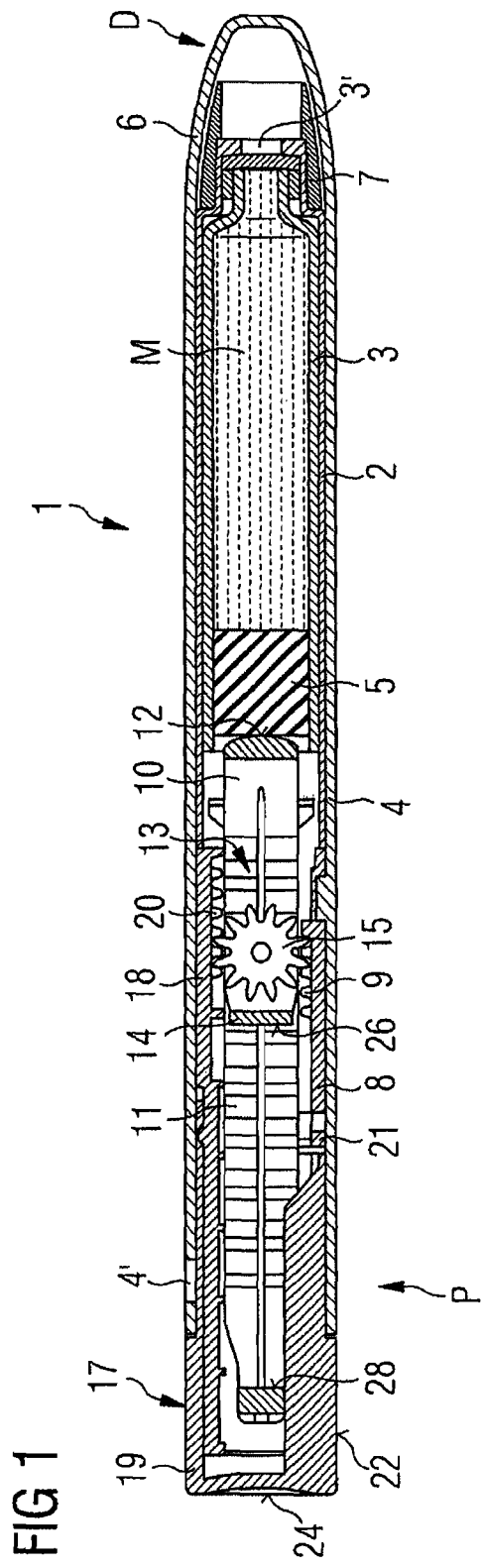
FIG. 1 shows a sectional view of an exemplary embodiment of a medication delivery device in a first, cartridge full, position.

According to a first aspect a medication delivery device comprises a housing having a proximal end and a distal end, a cartridge for holding a medication, the cartridge having an outlet, a moveable piston being retained within the cartridge, a drive member moveable in a proximal direction with respect to the housing for setting a dose of medication to be delivered and in a distal direction with respect to the housing for delivering the dose and a piston rod adapted to drive the piston in the distal direction with respect to the cartridge for delivering the dose. The drive member is releasably coupled to the piston rod. The medication delivery device further comprises a resilient member which is arranged to move the drive member in the proximal direction with respect to the housing after dose delivery, thereby reducing pressure of the piston rod on the piston.

This has the advantage that a simple and precise usage of the medication delivery device is enabled. A user may administer a number of pre-set doses of the medication. For example, when, after dose delivery, a force in the distal direction exerted on the drive member for dose delivery has been removed from the drive member, the drive member is moved in the proximal direction with respect to the housing due to the resilient member mechanically interacting with the drive member. The drive member may move in the axial direction with respect to the housing and/or rotate with respect to the housing. The proximal movement of the drive member may take place before the next dose is set. The piston rod may follow at least partly this movement of the drive member in the proximal direction. In particular, the drive member may be moved directly by the resilient member in the proximal direction with respect to the housing, whereas the piston rod may be moved indirectly by the resilient member via the movement of the drive member in the proximal direction with respect to the housing that is transferred to the piston rod. Thus, the piston rod may be moved relative to the piston in the proximal direction. Thereby, the distance between the piston rod and the piston may be increased. In this way, room is provided that allows a deformed piston, in particular an elastically deformed piston, to relax in the proximal direction after dose delivery.

Accordingly, after the piston rod has been moved proximally, the pressure exerted by the piston rod on the piston may be reduced or removed from the piston. Thus, the deformed piston may mainly relax in the proximal direction after dose delivery. Uncontrolled relaxation of the piston in the distal direction which may result in unintentionally dispensing medication from the cartridge may thus be reduced. Furthermore, an increased distance between the piston rod and the piston before setting a subsequent dose may result in reducing the risk of medication being unintentionally dispensed from the cartridge, due to vibrations, for example, as the mechanical connection between piston and piston rod is interrupted.

Overall, the dose accuracy may be improved by moving the piston rod in the proximal direction after dose delivery. Preferably, the piston rod is moved in the proximal direction after dose delivery only as far as it is required for allowing relaxation of the piston in the proximal direction.

The piston may comprise a deformable, preferably elastically deformable, for example compressible, material. For instance, the piston comprises rubber. During dose delivery, the piston may be deformed on account of the force transmitted from piston rod to piston in the distal direction for dose delivery. The piston may be compressed, for example. Deforming of the piston may result in a change of the volume of the piston or the volume of the piston may be constant during and/or after deformation.

After the force in the distal direction is removed from the piston, the deformed piston tends to return to its previous, i.e. undeformed shape. Thereby, the piston may exert pressure on the medication in the distal direction, which may result in medication being unintentionally dispensed from the cartridge after dose delivery should already be completed (weeping). Weeping may be considerably reduced, if the piston rod is moved in the proximal direction after dose delivery. For example, drugs such as heparin may cause visible bruising when making contact with the surface of the human body. By reducing or preventing weeping of the medication delivery device, the risk of visible bruising on the surface of a user's body may be reduced or prevented.

The piston rod may be retracted from the piston by mechanical energy which may be stored in the resilient member during dose delivery. No electric energy is required for this purpose.

In an advantageous embodiment the resilient member is arranged to move the drive member and thereby the piston rod in the proximal direction with respect to the housing after dose delivery such that the piston rod is moved away from the piston by a distance. It is preferred for this distance to be in the range of (about) 0.1 to 2.0 mm, in particular in the range of (about) 0.1 to 0.5 mm. A distance of this kind may be particularly expedient for providing sufficient room for relaxation of the piston in the proximal direction, in particular if the piston comprises rubber.

In a further advantageous embodiment the drive member is releasably coupled to the piston rod such that the piston rod follows movement of the drive member in the distal direction with respect to the housing for delivering the dose and does not follow movement of the drive member in the proximal direction with respect to the housing for setting the dose. Of course, the piston rod and the drive member are expediently coupled for the piston rod to follow proximal movement of the drive member with respect to the housing which is caused by mechanical interaction of drive member and resilient member after dose delivery and, in particular, before the next dose is set.

This has the advantage that a simple and precise usage of the medication delivery device by a user is enabled, for example to administer a number of pre-set doses of a medication with high dose accuracy. Thus, persons without formal medical training, i.e. patients, may administer accurate and predefined doses of the medication repeatedly.

In a further advantageous embodiment the drive member comprises a first rack and the piston rod is coupled to the first rack via a pinion, wherein the pinion is engaged with a second rack and the second rack is connected to the housing. The first rack of the drive member is expediently moveable with respect to the housing. Preferably, the first rack is axially movable between a first and a second end position.

In a further advantageous embodiment the drive member comprises a first supporting element and the piston rod is coupled to the first supporting element via a lever, wherein the lever is engaged with a second supporting element and the second supporting element is connected to the housing.

In a further advantageous embodiment the second rack or the second supporting element is formed unitarily with the housing or is secured against rotational and/or axial movement with respect to the housing.

In this way an advantageous coupling for actuation of the piston rod may be provided for.

In a further advantageous embodiment the resilient member is formed integrally with the housing or as a separate element, e.g. integrally with an insert of the housing.

In this way a precise and secure coupling of the resilient member to the housing may be provided for. Moreover, the resilient member and the housing are easily manufactured. Preferably, the insert of the housing is fixed to the housing. The insert may comprise the resilient member. For example, the resilient member is formed integrally with the insert of the housing, wherein the insert of the housing comprises the second rack in addition to the resilient member. Preferably, the resilient member is different from the piston.

In a further advantageous embodiment the resilient member is arranged to mechanically interact with the drive member at a distal end side of the drive member, in particular during dose delivery.

Thus, the resilient member may interact with the drive member to move the drive member in the proximal direction with respect to the housing after dose delivery in a simple way.

In a further advantageous embodiment the resilient member and the drive member are arranged for a force in the distal direction to be exerted on the resilient member during dose delivery such that the resilient member is biased in such a way that after dose delivery and after removing the force in the distal direction, the biased resilient member moves the drive member in the proximal direction with respect to the housing.

Thus, after having delivered the dose, the resilient member is adapted to move the drive member in the proximal direction with respect to the housing. For example, the resilient member is a spring, like a circular spring, a leaf spring or a coil spring. Preferably, the resilient member is deformed during the distal movement of the drive member during dose delivery, e.g. near the end of dose delivery, for storing mechanical energy for moving the drive member in the proximal direction.

According to a second aspect a method for operating the medication delivery device of the first aspect of the invention is provided. After having set a dose of medication by moving the drive member in the proximal direction and after having moved the drive member in the distal direction for delivering the dose by exerting a force acting on the drive member in the distal direction, wherein the force in the distal direction causes the piston rod to move in the distal direction with respect to the housing and the resilient member to be biased, the method comprises the steps of waiting for a preset period of time, and thereafter removing the force in the distal direction from the drive member with the drive member being moved in the proximal direction with respect to the housing by mechanical interaction of the biased resilient member and the drive member, which mechanical interaction causes movement of the piston rod in the proximal direction with respect to the housing.

This has the advantage that a simple and precise method for operating the medication delivery device is provided for. For example, a user may administer a number of pre-set doses of the medication. After dose delivery, when a distal force acting on the drive member has been removed, for example when a user has removed the finger from a dose button, the drive member may be moved in the proximal direction with respect to the housing due to interaction with the biased resilient member and, in particular, before the next dose is set, preferably subsequent to dose delivery. The piston rod may at least partly follow the movement of the drive member in the proximal direction. Thus, the piston rod may move with respect to the piston, thereby reducing pressure of the piston rod on the piston and possibly increasing the distance between piston rod and piston. Accordingly, the piston may mainly relax in the proximal direction.

The distal force acting on the drive member is expediently removed before a subsequent dose of the medication is set, preferably subsequent to dose delivery, causing the piston rod to be moved in the proximal direction with respect to the housing by mechanical interaction of the resilient member and the drive member. After having moved the drive member distally and into abutment with one end of the resilient member during dose delivery, and preferably biasing the resilient member upon further distal movement, the biased resilient member may exert a proximal force on the drive member, i.e. a force acting in the proximal direction on the drive member. The distal force acting on the drive member, e.g. exerted by a user, during dose delivery is expediently greater than the proximal force exerted by the resilient member on the drive member. Thus, if the distal force on the drive member is removed after dose delivery, the (relaxing) resilient member may move the drive member in the proximal direction with respect to the housing. It should be noted that the method recited above may be carried out without interaction of medication and human body.

In an advantageous embodiment the piston is elastically deformed during movement of the piston rod in the distal direction and the piston starts to resume its undeformed shape by relaxing in the distal direction during the preset period of time thereby expelling further medication from the cartridge. Preferably, the piston continues to resume its undeformed shape by relaxing (essentially) in the proximal direction after the piston rod has been moved in the proximal direction with respect to the housing.

By waiting for the preset period of time, the deformed piston is given time to relax in the distal direction before the pressure of the piston rod on the piston is removed. Relaxation in the distal direction causes further medication to be expelled from the cartridge. It is therefore preferred for the amount of medication which is expelled during the preset period to be part of the dose. A deformed piston tends to return to its previous shape more quickly soon after the distal movement of the drive member for dose delivery is finished. Later on, relaxation is slowed down. Therefore, it is advisable to wait the preset period of time after distal movement of the drive member and the piston rod for dose delivery has been completed and to regard the amount of medication expelled to be part of the (pre-set) dose. Dose accuracy can be increased in this way.

After the piston has relaxed partly in the distal direction and, thereafter, the distal force on the drive member has been removed, the piston may (essentially) relax in the proximal direction.

In an advantageous embodiment the preset period of time is greater than or equal to 5 seconds and less than or equal to 15 seconds, e.g. 10 seconds.

In a further advantageous embodiment a restriction member limits that movement of the drive member in the proximal direction with respect to the housing, which is caused by the resilient member. The restriction member may be arranged to mechanically interact with the drive member for this purpose.

Uncontrolled proximal movement of the drive member after dose delivery is avoidable in this way. A detent as a restriction member may limit the movement of the drive member in the proximal direction caused by interaction of drive member and resilient member, for example. When a subsequent dose of medication to be delivered is set, the drive member can be moved in the proximal direction with respect to the housing, wherein the proximal force applied by a user to the drive member may easily overcome the resistance provided by the restriction member. In contrast thereto, movement of the drive member in the proximal direction which is caused by interaction of drive member and resilient member preferably doesn't overcome the resistance provided by the restriction member.

In a further advantageous embodiment the distance which the drive member is moved in the proximal direction with respect to the housing after dose delivery caused by the resilient member is less than the distance the drive member is movable in the proximal direction for setting a (subsequent) dose of medication to be delivered.

The term "medication delivery device" may mean a single-dose or multi-dose or pre-set dose or pre-defined, disposable or re-useable device designed to dispense a user selectable or pre-defined dose of a medication, for example 7 multiple pre-defined doses. The medication may comprise insulin, growth hormones, low molecular weight heparins, and/or their analogues and/or derivatives etc. Said device may be of any shape, e.g. compact or pen-type. Furthermore, the said device may comprise a needle or may be needle-free. In particular, the term "medication delivery device" may mean a disposable needle-based pen-type device providing multiple pre-defined doses having mechanical and manual dose delivery and dose setting mechanisms, which is designed for use by persons without formal medical training such as patients. Preferably, the medication delivery device is of the injector-type.

The term "housing" may mean any exterior housing ("main housing", "body", "shell") or interior housing ("insert", "inner body") having a unidirectional axial coupling to prevent proximal movement of specific components. The housing may be designed to enable the safe, correct, and comfortable handling of the medication delivery device or any of its mechanism. Usually, it is designed to house, fix, protect, guide, and/or engage with any of the inner components of the medication delivery device (e.g., cartridge, piston, piston rod) by limiting the exposure to contaminants, such as liquid, dust, dirt etc. In general, the housing may be unitary or a multipart component of tubular or non-tubular shape. Preferably, the exterior housing is provided with a plurality of maximum dose stops adapted to be abutted by an axial stop provided on the drive member.

The term "engaged" may particularly mean the interlocking of two or more components of the medication delivery device, e.g. a spline, thread, or meshed teeth connection, preferably the interlocking of meshed teeth of components.

The term "drive member" may mean any component adapted to operate through/within the housing, designed to transfer axial movement through/within the medication delivery device, preferably from an actuation means to the piston rod. In a preferred embodiment the drive member is further releasably coupled with the piston rod. The drive member may be of unitary or multipart construction.

The term "releasably coupled" may preferably mean that two components of instant device are joined for transfer of force or movement in one direction only, preferably during dispense. Preferably, the drive member is releasably coupled to the piston rod such that the piston rod follows movement of the drive member in the distal direction with respect to the housing for delivering the dose and does not follow movement of the drive member in the proximal direction with respect to the housing for setting the dose. The piston rod and the drive member are expediently coupled for the piston rod to follow proximal movement of the drive member with respect to the housing which is caused by mechanical interaction of drive member and resilient member after dose delivery and, in particular, before the next dose is set.

The term "piston rod" may mean a component adapted to operate through/within the housing, designed to transfer axial movement through/within the medication delivery device, preferably from the drive member to the piston, for the purpose of discharging/dispensing an injectable product. Said piston rod may be flexible or rigid. It may be a simple rod, a lead-screw, a rack and pinion system, a worm gear system, or the like. The term "piston rod" may further mean a component having a circular or non-circular cross-section. It may be made of any suitable material known by a person skilled in the art and may be of unitary or multipart construction. Preferably, the piston rod comprises a series of one or more sets of longitudinally spaced ribs and/or indentations.

The term "pinion" may mean a toothed wheel used in conjunction with a rack, preferably a rack to transmit force and/or motion. Preferably, the term "pinion" means a pinion mounted within a carrier.

The term "lever" may mean any beam component pivoted about a fulcrum to transmit force and/or motion. In a preferred embodiment the fulcrum point is located on the housing and load is applied through the drive member. In yet another preferred embodiment the term "lever" may mean any beam component that is pivoted essentially proximally with respect to the piston rod during dose setting and that is pivoted essentially distally with respect to the piston rod during dose delivery. For example, a lever assembly may mean any component consisting of a lever and a carrier designed to transmit force and/or motion.

The term "rack" may mean any component having a linear array of ribs and/or indentations and/or teeth. In a preferred embodiment a rack is located in the housing and a further rack is located in the drive member. In a further preferred embodiment one and/or both, more preferably one, of the racks located on the housing or on the drive member is flexible and/or pivoted and/or movable in one or more axis, more preferably one.

The "distal end" of the device or a component of the device may mean the end, which is closest to the dispensing end of the device.

The "proximal end" of the device or a component of the device may mean the end, which is furthest away from the dispensing end of the device.

Exemplary embodiments are explained in the following with the aid of schematic drawings.

FIG. 1 shows a sectional view of a medication delivery device 1 in a first, cartridge full, position.

The medication delivery device 1 comprises a cartridge housing 2 and a cartridge 3. The cartridge 3 is retained within the cartridge housing 2. The cartridge has an outlet 3'. The device 1 comprises a main (exterior) housing 4 having a proximal end P and a distal end, which is closest to the dispensing end D of the medication delivery device 1. The proximal end of the cartridge housing 2 and the distal end of the main housing 4 are secured together by any suitable means known to the person skilled in the art. In the illustrated embodiment, the cartridge housing 2 is secured within the distal end of the main housing 4.

The cartridge 3 from which a number of doses of a medication M may be dispensed is provided in the cartridge housing 2. A piston 5 is retained in the proximal end of the cartridge 3. A removable cap 6 is releasably retained over the distal end of the cartridge housing 2. The removable cap 6 may be optionally provided with one or more windows to the cartridge 6' through which the position of the piston 5 within the cartridge 3 can be viewed.

Figure 1A:
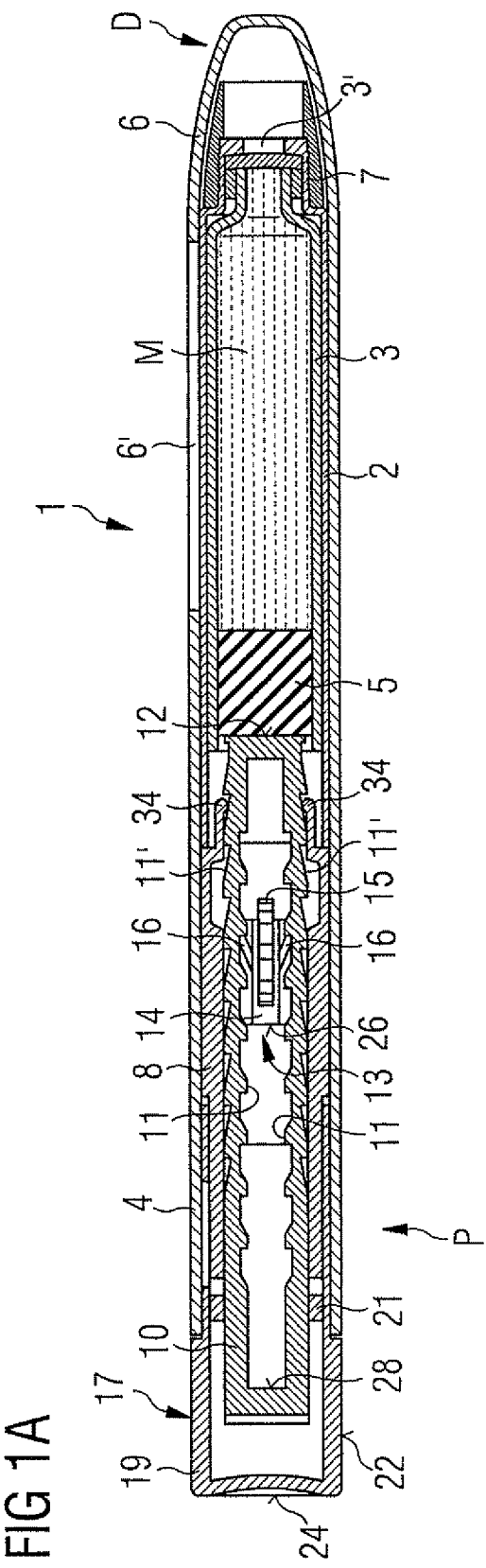
FIG. 1A shows a further sectional view of the medication delivery device in the first, cartridge full, position.

In the illustrated embodiment, the distal end of the cartridge housing 2 is provided with a distal threaded region 7 designed for the attachment of a suitable needle assembly to enable medication to be dispensed from the cartridge 3. In the illustrated embodiment, the main housing part 3 is provided with an insert, i.e. internal housing 8. The internal housing 8 is secured against rotational and axial movement with respect to the main housing 4. The internal housing 8 is provided with a second rack 9 extending along the main axis of the internal housing 8. Alternatively, the second rack 9 may be formed unitarily with the main housing 4. Alternatively, the internal housing 8 may be formed integrally with the main housing 4. Additionally, the internal housing 8 is provided with a plurality of guide lugs 32 (cf. FIG. 4) and pawl means 34 (cf. FIGS. 1A and 4). The pawl means 34 may be an integrated part of the internal housing 8 or may be a separate component.

A piston rod 10 extending through the main housing 4 has a first set of indentations 11' (cf. FIG. 1A) extending longitudinally along external surfaces of the piston rod 10. In particular, the piston rod 10 is designed and arranged to be secured against rotational movement with respect to the main housing 4. A second set of indentations 11 extends longitudinally along internal surfaces of the piston rod 10. The first set of indentations 11' of the piston rod 10 extends through and is engaged with the pawl means 34 provided on the internal housing 8, for example on or connected to the second rack 9, to prevent movement of the piston rod 10 in the proximal direction with respect to the housing during setting of the dose. A bearing surface 12 located at the distal end of the piston rod 10 is disposed to abut a proximal face of the piston 5. In the illustrated embodiment the longitudinal spacing of the first set of indentations and the second set of indentations 11 is essentially equal.

A pinion gear 13, consisting of a carrier 14 and a pinion 15, free to rotate within the carrier 14, is located within a channel within the piston rod 10. Pawl arms 16 (FIG. 1A) located on the carrier 15 are releasably engaged with the second set of indentations 11 of the piston rod 10. The pawl arms 16 of the carrier 14 are designed to transmit force to the piston rod 10 in the distal direction during dispense and to allow relative movement between the pinion gear 13 and the piston rod 10 in the proximal direction during setting the dose. The teeth of the pinion 15 are permanently engaged with the teeth of the second rack 9 of the internal housing 8.

A drive member 17 extends about the piston rod 10 and is releasably coupled to the piston rod 10. The drive member 17 comprises a rack part 18 and an activation part 19. The rack part 18 and the activation part 19 are secured to each other to prevent rotational and axial movement there between. Alternatively, the drive member 17 may be a unitary component consisting of an integrated rack part 18 and activation part 19.

The rack part 18 is provided with a first rack 20 extending along the main axis of the rack part 18. The teeth of the first rack 20 of the rack part 18 are permanently engaged with the teeth of the pinion 15.

The drive member 17 has a plurality of guide slots (not shown) in which the guide lugs 32 (cf. FIG. 4) of the internal housing 8 are located. These guide slots define the extent of permissible axial movement of the drive member 17 with respect to the housing 4. In the illustrated embodiment the guide slots also prevent rotational movement of the drive member 17 relative to the main housing 4.

The medication delivery device 1 further comprises a resilient member 21. The resilient member 21 is arranged to move the drive member 17, preferably to move the drive member 17 and the piston rod 10 together, in the proximal direction with respect to the main housing 4 after dose delivery, thereby reducing or even removing pressure of the piston rod 10 on the piston 5. The resilient member 21 is arranged to mechanically interact with the drive member 17 at a distal end side of the drive member 17. In this exemplary embodiment, the resilient member 21 is formed integrally with the internal housing 8. Alternatively, the resilient member 21 may be formed integrally with the main housing 4. In another embodiment, the resilient member may be an element separate from the housing and from the internal housing. For example, the resilient member 21 is a spring, for instance a circular spring, a leaf spring or a coil spring.

The activation part 19 of the drive member 17 has a plurality of grip surfaces 22 and a dispensing face 24. To increase intuitiveness of the operation of the medication delivery device 1 and to indicate visual feedback regarding dose setting, the main housing 4 may optionally be provided with a window to the drive member 4' through which graphical status indicators provided on the drive member 17 can be viewed.

In the following, the operation of the medication delivery device 1 will be described.

To set a dose a user grips the grip surfaces 22 of the drive member 17. The user then pulls the drive member 17 in a proximal direction away from the main housing 4 thereby moving the rack part 18 in a proximal direction. The proximal movement of the rack part 18 causes the pinion 15 to rotate and move proximally by virtue of the engagement of the teeth of the pinion 15 of the pinion gear 13 with the teeth of the first rack 20 of the rack part 18 and the teeth of the second rack 9 of the internal housing 8 thus moving the pinion gear 13 in the proximal direction.

The piston rod 10 is prevented from moving proximally by interaction of pawl means 34 of the internal housing 8 with the first set of indentations 11' on the piston rod 10 during dose setting. As the drive member 17 travels in the proximal direction relative to the piston rod 10, the pawl arms 16 of the carrier 14 are elastically displaced inwardly by interaction with the second set of indentations 11 of the piston rod 10.

Figure 2:
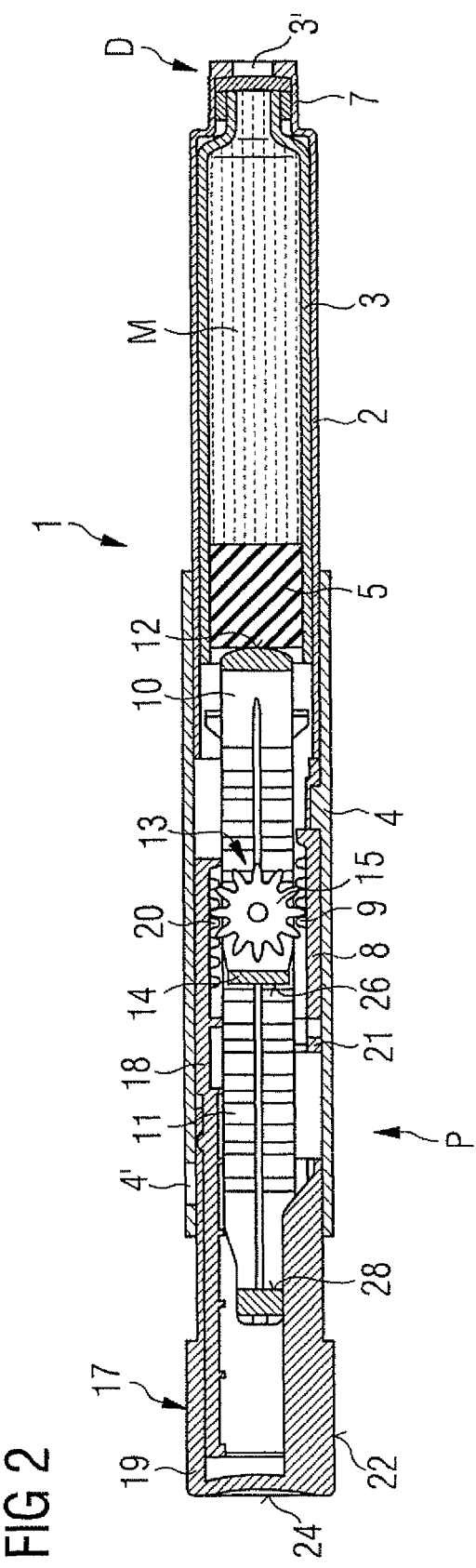
FIG. 2 shows a sectional view of the medication delivery device in a second, first dose set, position.

The proximal travel of the drive member 17 is limited by the guide slots of the rack part 18. At the end of the travel of the drive member 17, the pawl arms 16 of the carrier 14 engage with the next sequential indentation of the second set of indentations 11 of the piston rod 10 as indicated in FIG. 2. The action of the pawl arms 16 of the carrier 14 positively engaging the second set of indentations 11 of the piston rod 10 creates an audible and tactile feedback to the user to indicate that the dose has been set.

When the dose has been set, the user may then dispense this dose by depressing the dispensing face 24 of the activation part 19 of the drive member 17. By this action the drive member 17 and the rack part 18 are moved axially in the distal direction relative to the main housing 4. As the teeth of the pinion 15 of the pinion gear 13 are engaged with the teeth of the first rack 20 of the rack part 18 and the teeth of the second rack 9 of the internal housing 8, the pinion 15 of the pinion gear 13 is caused to rotate and move in the distal direction thus moving the pinion gear 13 longitudinally in the distal direction. As the pawl arms 16 of the carrier 14 of the pinion gear 13 are engaged with the second set of indentations 11 of the piston rod 10, the piston rod 10 is caused to move longitudinally in the distal direction with respect to the internal housing 8.

The distal axial movement of the piston rod 10 causes the bearing surface 12 of the piston rod 10 to bear against the piston 5 in the cartridge 3 causing the piston 5 to be deformed and moved distally, thereby causing a dose of medicament to be dispensed through the attached needle (not explicitly shown).

The distal travel of the drive member 17 is limited by the guide slots (not explicitly shown) of the rack part 18. Audible and tactile feedback to indicate that the dose has been dispensed is provided by the interaction of the pawl means 34 of the internal housing 8 with the first set of indentations 11' of the piston rod 10. Additionally, visual feedback regarding dose dispense may optionally be indicated by a graphical status indicator, provided on the drive member 17, which can be viewed through the optional window to the drive member 4' in the main housing 4.

Figure 3:
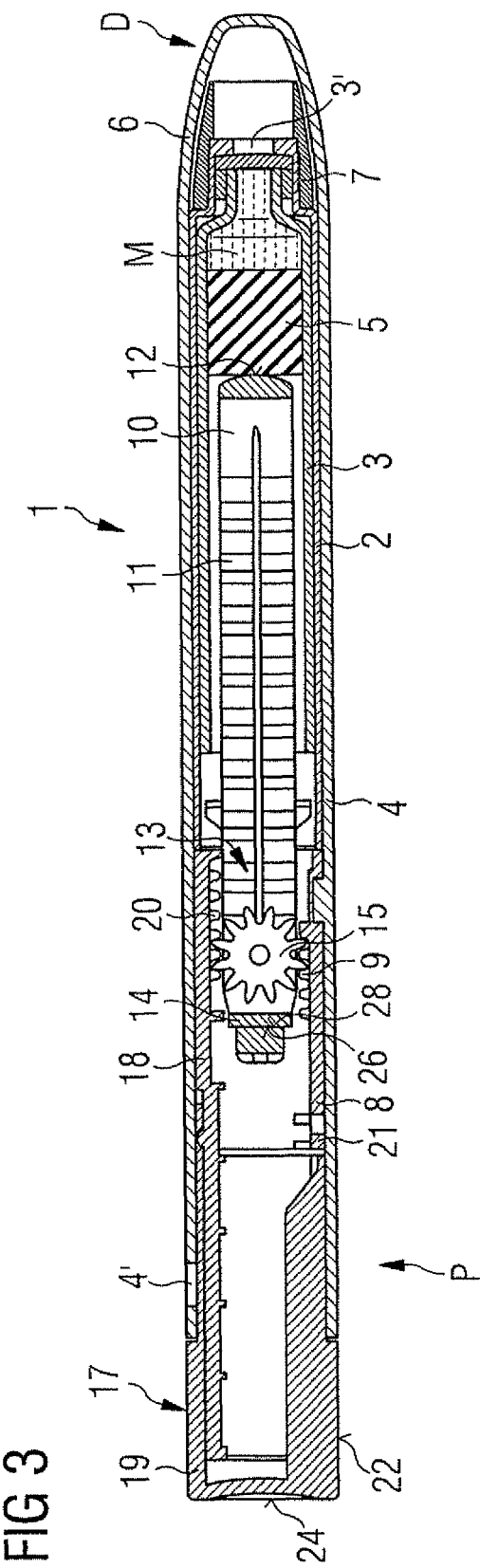
FIG. 3 shows a sectional view of the medication delivery device in a third, final dose dispensed, position.

Further doses may be delivered as required up to a predetermined maximum number of doses. FIG. 3 shows the medication delivery device 1 of instant invention in a condition where the maximum number of doses has been delivered. In this condition a proximal face 26 of the carrier 14 abuts an internal distal face 28 of the piston rod 10 to prevent further axial movement of the pinion gear 13 and thus the drive member 17 in proximal direction.

After distal movement of the drive member 17 for dose delivery is finished, the resilient member 21 has been biased. For example, a distal end face of the drive member may have moved into abutment with the resilient member 21 and the drive member 17 may have been moved further into the distal direction together with the resilient member 21, thereby biasing the resilient member 21. After the user removes the force acting on the drive member 17 in the distal direction, the biased resilient member 21 moves the drive member 17 and the piston rod 10 in the proximal direction with respect to the main housing 4. Thereby, pressure of the piston rod 10 on the piston 5 is reduced as the piston rod is retracted from the piston. In this way, room for relaxation of the piston in the proximal direction may be provided. Relaxation of the piston 5 in the distal direction may be reduced or avoided in this way. Correspondingly, unintentional weeping of the device may be reduced.

Preferably, the piston rod 10 is moved away from the piston 5 by a distance and/or the drive member 17 is moved by a distance in the range of (about) 0.1 to 2.0 mm, in particular in the range of (about) 0.1 to 0.5 mm, in the proximal direction with respect to the main housing 4 by means of the resilient member 21 moving the drive member 17 in the proximal direction after dose delivery. The distance the drive member 17 is moved does not have to be the same as the distance the piston rod 10 is moved, i.e. the piston rod 10 and the drive member 17 may be coupled with mechanical advantage.

A restriction member 30 (cf. FIGS. 4, 6A, 6B), for example one of or a plurality of detents, may limit that movement of the drive member 17 in the proximal direction with respect to the main housing 4, which is caused by the resilient member 21. The restriction member 30 may be provided on or secured to the housing. When the next dose of medication M to be delivered is set, the drive member 17 can be moved in the proximal direction with respect to the housing 4, wherein a proximal force applied by a user of the medication delivery device 1 may easily overcome the resistance against proximal movement of the drive member 17 which is provided by the restriction member 30. Uncontrolled proximal movement of the drive member 17 by means of the resilient member 21 may be avoided by the restriction member 30.

After the distal movement of the drive member 17 for dose delivery has been finished and after the resilient element has been biased, it is preferred for a user of the medication delivery device 1 to wait for a preset period of time, during which period he holds the drive member 17 in the distal end position, and only thereafter to remove the force acting in the distal direction on the drive member. This is of particular advantage, if the piston 5 is elastically deformed, e.g. compressed, during dose delivery on account of the pressure exerted on the piston 5 by the piston rod 10. For the time immediately after the end of the distal movement of the piston rod 10 for dose delivery, the amount that the piston 5 relaxes is usually the highest. A compressed piston often relaxes exponentially. Thus, it is advantageous to allow the piston 5, at first, to relax in the distal direction. The amount of medication expelled during relaxation in the distal direction may be part of the dose. Therefore, it is advisable to leave a needle of the device in the body for the preset period of time, if the medication is injected into a body by the user. After the preset period of time has lapsed, the distal force is removed from the drive member 17 and, on account of the biased resilient member 21, the drive member 17 and the piston rod 10 are moved in the proximal direction, thereby allowing the piston 5 to finish relaxation mainly in the proximal direction.

The preset period of time may be greater than or equal to 5 seconds and less than or equal to 15 seconds, e.g. 10 seconds. As the amount the piston is compressed may depend on the force which is applied, waiting for the preset amount of time after distal movement of the drive member has been finished has the advantage that dose accuracy is increased as initial relaxation of the piston after the distal movement of the drive member has stopped contributes to dose delivery. The distance the drive member 17 is moved in the proximal direction with respect to the main housing 4 after dose delivery due to interaction of drive member 17 and resilient member 21 is expediently smaller than the distance the drive member 17 is moved in the proximal for setting the dose of medication M to be delivered.

In the illustrated embodiment, the medication delivery device 1 is a fixed dose pen. Alternatively, the medication delivery device 1 may be a pen for delivering variable, preferably user-settable doses.

Figure 4:
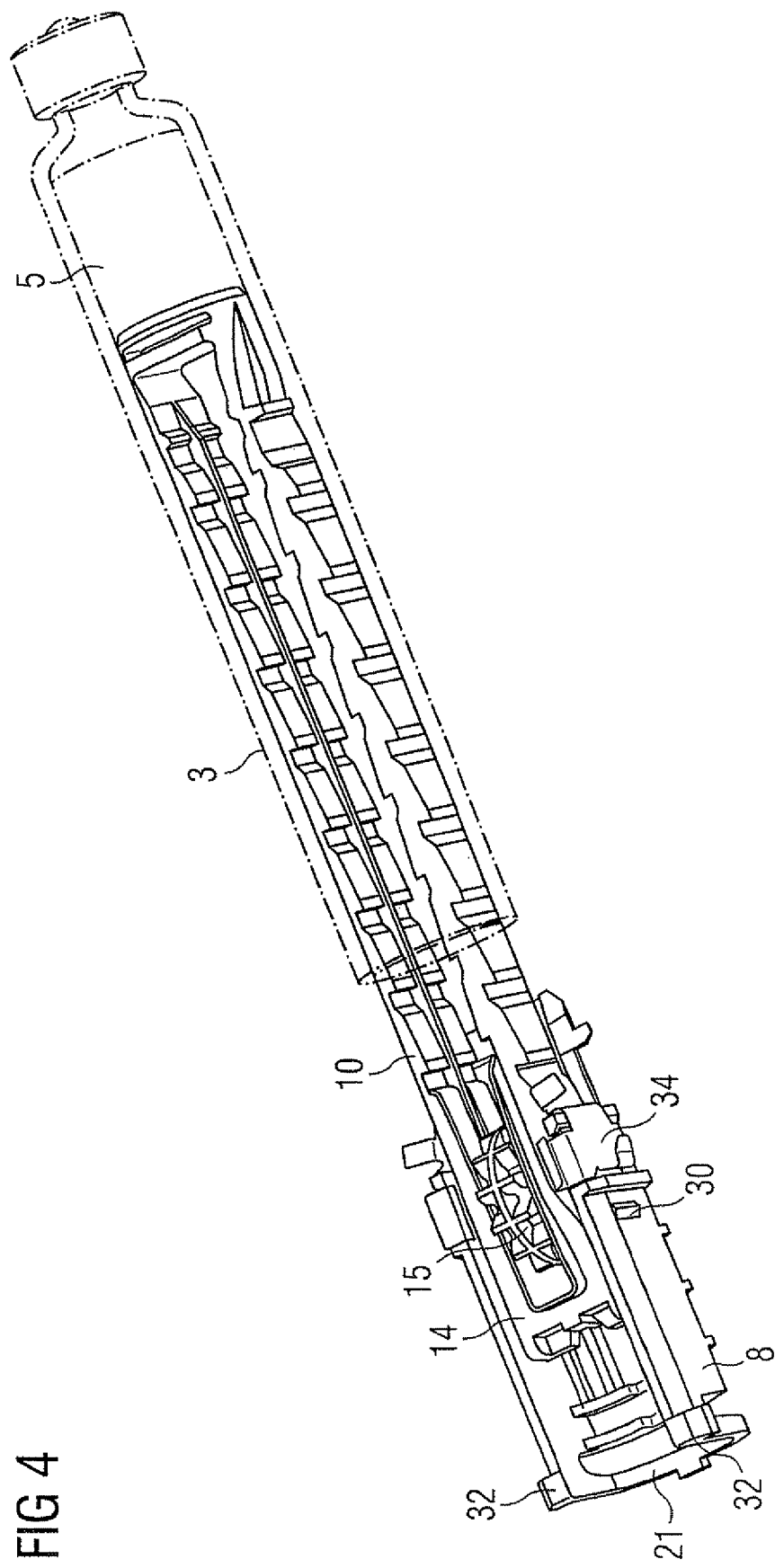
FIG. 4 shows a 3-dimensional view of a part of the medication delivery device.

FIG. 4 shows a 3-dimensional view of a part of the medication delivery device 1.

The resilient member 21 of the medication delivery device 1 is arranged to move the drive member 17 (cf. FIG. 1) in the proximal direction with respect to the main housing 4 after dose delivery. The resilient member 21 is arranged to mechanically interact with the drive member 17 at a distal end side of the drive member 17. In this exemplary embodiment, the resilient member 21 is formed integrally with the internal housing 8. A proximal end face of the internal housing 8, which comprises the second rack 9, comprises the resilient member 21. The resilient member abuts the activation part 19 of the drive member 17 near the end of dose delivery and is bent in the distal direction while the drive member is moved further in the distal direction, thereby biasing the resilient member. The resilient member 21 is designed as a flexible, e.g. U-shaped, region of the internal housing 8. When the user removes the distal force from the activation part 19, the resilient member 21 relaxes in the proximal direction and moves the drive member 17 in the proximal direction. The drive member 17 may be moved proximally until the drive member 17 engages the restriction member 30, for example one of or a plurality of detents.

Movement of the drive member 17 in the proximal direction results in the piston rod 10, which is coupled to the drive member via the carrier 14 and the pinion 15, being moved in the proximal direction and away from the piston 5.

Figure 5:
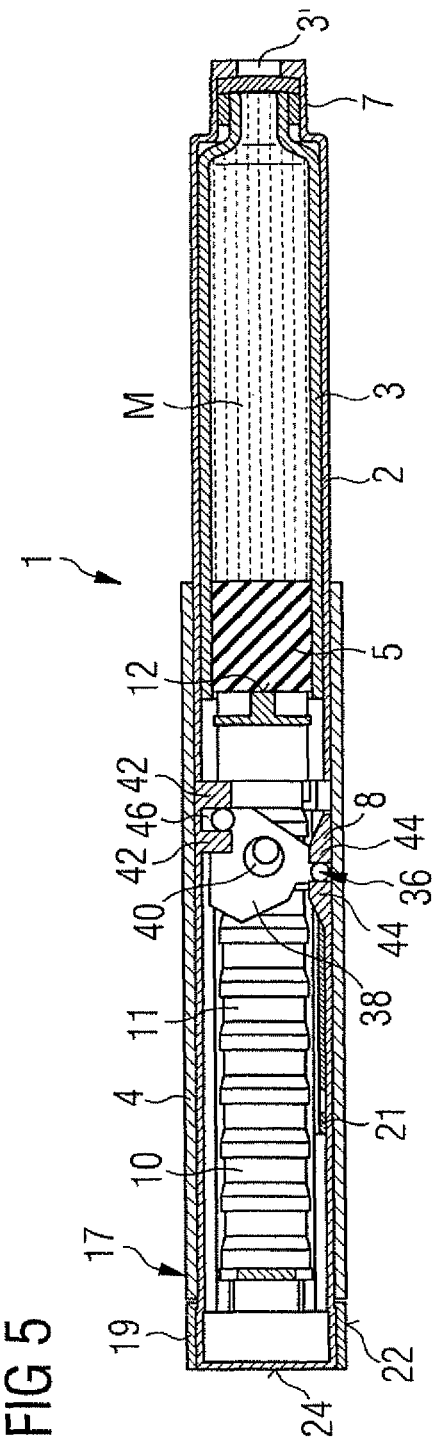
FIG. 5 shows a sectional view of a further exemplary embodiment of the medication delivery device.

FIG. 5 shows a sectional view of a further exemplary embodiment of a medication delivery device 1. The illustrated medication delivery device 1 comprises a further actuation mechanism of the piston rod 10.

The internal housing 8 is provided with a fulcrum point 36 for attaching a lever 38. Alternatively, the internal housing 8 may be formed integrally with the main housing 4. The lever 38 comprises one or a plurality of lugs 40. The lever 38 is located within a channel of the main housing 4. The lugs 40 of the lever 38 are releasably coupled with the first set of indentations 11 of the piston rod 10. The first set of indentations 11 is designed to allow force transmission to the piston rod 10 in the distal direction during dose delivery and to allow relative movement between the lever 38 and the piston rod 10 in the proximal direction during setting of the dose. The drive member 17 comprises a first supporting element 42 and the piston rod 10 is coupled to the first supporting element 42 via the lever 38, wherein the lever 38 is engaged with a second supporting element 44 being connected to the housing 4. The second supporting element 44 is attached to the fulcrum point 36 of the internal housing 8 for pivotable movement between the lever 38 and the internal housing 8.

The drive member 17 comprises a slot 46 and the activation part 19, wherein the slot 46 and the activation part 19 are secured to each other to prevent rotational and/or axial movement there between. Alternatively, the drive member 17 may be a unitary component consisting of the integrated slot 46 and the activation part 19. The first supporting element 42 is located within the slot 46 of the drive member 17. The slot 46 of the drive member 17 is designed to allow transverse movement, but not longitudinal movement, of the first supporting element 42 relative to the drive member 17.

Further parts of the design and the mechanism of the medication delivery device 1 correspond to the above mentioned embodiment of the medication delivery device 1.

Figure 6A:
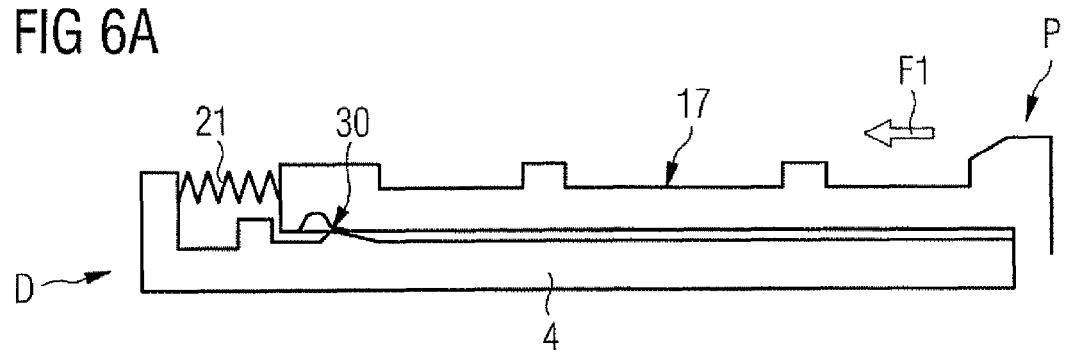
FIGS. 6A and 6B show a sectional view of a schematic illustration of the medication delivery device.
Figure 6B:
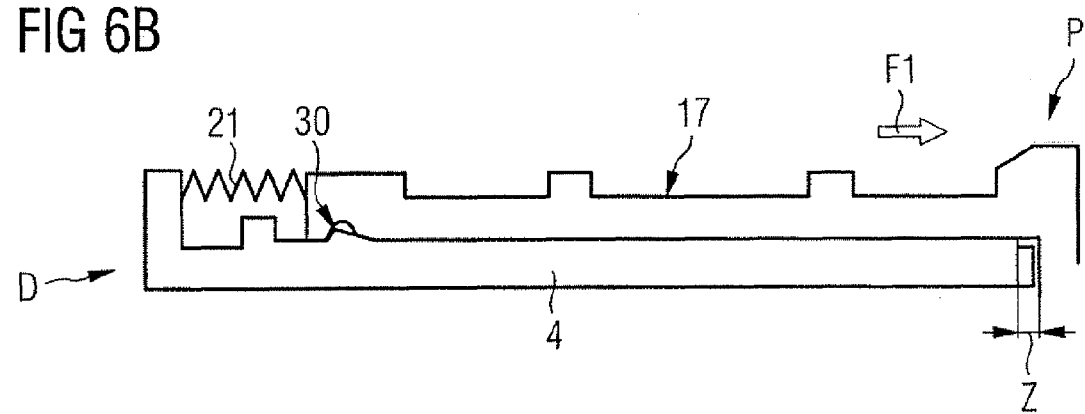

FIGS. 6A and 6B show a sectional view of a simplified, schematic illustration of a part of the medication delivery device 1 to further illustrate the operating mode of the medication delivery device 1.

For setting a dose of medication to be delivered, the drive member 17 is moved in the proximal direction with respect to the housing 4. During delivery of the dose of medication, the drive member 17 is moved in the distal direction with respect to the housing 4 by a first distal force F1 a user applies to the drive member 17 (cf. FIG. 6A). The piston 5 (not explicitly shown) may be compressed during dose delivery due to the medication in the cartridge and the force F1 acting on the piston 5 from opposite sides of the piston. Moreover, the resilient member 21, for example a spring, and the drive member 17 are arranged for the first force F1 also acting on the resilient member 21 during dose delivery. In this way, the resilient member 21 is biased such that after dose delivery and after having removed the first force F1 from the drive member 17 in the distal direction, the biased resilient member 21 exerts a second force F2 on the drive member 17 and moves the drive member 17 in the proximal direction with respect to the housing 4. Accordingly, the drive member is moved by a distance Z with respect to the housing 4. The pressure of the piston rod 10 (not explicitly shown) on the piston 5 may be reduced in this way and relaxation of the piston 5 in the proximal direction is facilitated. For example, the distance Z may be in the range of about 0.1 to 2.0 mm, preferably 0.1 to 0.5 mm.

Thus, the piston 5 may relax essentially in the proximal direction after dose delivery and after having removed the first force F1, the second force F2 causing movement of the piston rod 10 away from the piston 5.

Preferably, the resilient member 21 is biased, e.g. by deformation and/or compression, during the distal movement of the drive member 17, in particular near the end of distal movement of the drive member for dose delivery.

Devices similar to the ones described above are described in WO 2008/058666 A1, the disclosure content being explicitly incorporated by reference into the present application.

As previously discussed, a first aspect of the invention provides a medication delivery device (1) comprising
- a housing (4) having a proximal end (P) and a distal end (D),
- a cartridge (3) for holding a medication (M), the cartridge (3) having an outlet (2),
- a moveable piston (5) being retained within the cartridge (3),
- a drive member (17) moveable in a proximal direction with respect to the housing (4) for setting a dose of medication (M) to be delivered and in a distal direction with respect to the housing (4) for delivering the dose and a piston rod (10) adapted to drive the piston (5) in the distal direction with respect to the cartridge (3) for delivering the dose, the drive member (17) being releasably coupled to the piston rod (10) characterized in that the medication delivery device (1) further comprises a resilient member (21) which is arranged to move the drive member (17) in the proximal direction with respect to the housing (4) after dose delivery, thereby reducing pressure of the piston rod (10) on the piston (5).

A second aspect provides a method for operating the medication delivery device (1) according to the first aspect, and third through ninth aspects, discussed below, wherein after having set a dose of medication (M) by moving the drive member (17) in the proximal direction and after having moved the drive member (17) in the distal direction for delivering the dose by exerting a force acting on the drive member (17) in the distal direction, wherein the force in the distal direction causes the piston rod (10) to move in the distal direction with respect to the housing (4) and the resilient member (21) to be biased, the method comprises the steps of waiting for a preset period of time, and thereafter removing the force in the distal direction from the drive member (17) with the drive member (17) being moved in the proximal direction with respect to the housing (4) by mechanical interaction of the biased resilient member (21) and the drive member (17), which mechanical interaction causes movement of the piston rod (10) in the proximal direction with respect to the housing.

A third aspect provides a medication delivery device (1) according to the first aspect, characterized in that the resilient member (21) is arranged to move the drive member (17) and thereby the piston rod (10) in the proximal direction with respect to the housing (4) after dose delivery such that the piston rod (10) is moved away from the piston (5) by a distance in the range of 0.1 to 2.0 mm.

A fourth aspect provides a medication delivery device (1) according to the first or third aspect, characterized in that the drive member (17) is releasably coupled to the piston rod (10) such that the piston rod (10) follows movement of the drive member (17) in the distal direction with respect to the housing (4) for delivering the dose and does not follow movement of the drive member (17) in the proximal direction with respect to the housing (4) for setting the dose.

A fifth aspect provides medication delivery device (1) according to any one of the first, third or fourth aspects, characterized in that the drive member (17) comprises a first rack (20) and the piston rod (10) is coupled to the first rack (20) via a pinion (15), wherein the pinion (15) is engaged with a second rack (9) and the second rack (9) is connected to the housing (4).

A sixth aspect provides a medication delivery device (1) according to any one of first, third or fourth aspect, characterized in that the drive member (17) comprises a first supporting element (42) and the piston rod (10) is coupled to the first supporting element (42) via a lever (38), wherein the lever (38) is engaged with a second supporting element (44) and the second supporting element (44) is connected to the housing (4).

A seventh aspect provides a medication delivery device (1) according to the fifth or sixth aspect, characterized in that the second rack (9) or the second supporting element (44) is formed unitarily with the housing (4) or is secured against rotational and/or axial movement with respect to the housing (4).

An eighth aspect provides a medication delivery device (1) according to any one of the first, or third through seventh aspects, characterized in that the resilient member (21) is formed integrally with the housing (4) or integrally with an insert (8) of the housing (4).

A ninth aspect provides a medication delivery device (1) according to any one of the first, or third through eighth aspects, characterized in that the resilient member (21) is arranged to mechanically interact with the drive member (17) at a distal end of the drive member (17).

A tenth aspect provides a medication delivery device (1) according to any one of the first or third through ninth aspects, characterized in that the resilient member (21) and the drive member (17) are arranged for a force in the distal direction to be exerted on the resilient member (21) during dose delivery such that the resilient member (21) is biased in such a way that after dose delivery and after removing the force in the distal direction, the biased resilient member (21) moves the drive member (17) in the proximal direction with respect to the housing (4).

An eleventh aspect provides a method according to the second aspect, wherein the piston (5) is elastically deformed during movement of the piston rod (10) in the distal direction and wherein the piston (5) starts to resume its undeformed shape by relaxing in the distal direction during the preset period thereby expelling medication (M) from the cartridge (3).

A twelfth aspect provides a method according to the eleventh aspect, wherein the piston (5) continues to resume its undeformed shape by relaxing in the proximal direction after the piston rod (10) has been moved in the proximal direction.

A thirteenth aspect provides a method according to the second, eleventh or twelfth aspect, wherein the preset period of time is greater than or equal to 5 seconds and less than or equal to 15 seconds.

A fourteenth aspect provides a method according to any one of the second, or eleventh through thirteenth aspects, wherein a restriction member (30) limits that movement of the drive member (17) in the proximal direction with respect to the housing (4), which is caused by the resilient member (21).

A fifteenth aspect provides a method according to any one of the second or eleventh through fourteenth aspects, wherein the distance the drive member (17) is moved in the proximal direction with respect to the housing (4) after dose delivery caused by the resilient member (21) is smaller than the distance the drive member (17) is movable in the proximal direction for setting the dose of medication (M) to be delivered.

REFERENCE SIGNS 1 medication delivery device
2 cartridge housing
3 cartridge
3' outlet (of cartridge)
4 (main) housing
4' window to drive member
5 piston
6 removable cap
6' window to cartridge
7 threaded region
8 internal housing (insert)

9 second rack
10 piston rod
11, 11' indentations (of piston rod)
12 bearing surface
13 pinion gear
14 carrier
15 pinion
16 pawl arms
17 drive member
18 rack part (of drive member)
19 activation part
20 first rack (of rack part)
21 resilient member
22 grip surface
24 dispensing face
26 proximal face of carrier
28 distal face of piston rod
30 restriction member
32 guide lug
34 pawl means
36 fulcrum point
38 lever
40 lug (of lever)
42 first supporting element
44 second supporting element
46 slot (of drive member)
D dispensing end
F1 first force
F2 second force
M medication
P proximal end
Z distance

What is claimed is:

1. A medication delivery device comprising
a housing having a proximal end (P) and a distal end (D),
a cartridge for holding a medication (M), the cartridge having an outlet,
a moveable piston being retained within the cartridge,
a drive member moveable in a proximal direction with respect to the housing for a dose of medication (M) to be delivered and in a distal direction with respect to the housing for delivering the dose and
a piston rod adapted to drive the piston in the distal direction with respect to the cartridge for delivering the dose,
the drive member being releasably coupled to the piston rod
characterized in that
the medication delivery device (1) further comprises a resilient member which is arranged to move the drive member in the proximal direction with respect to the housing after dose delivery, thereby reducing pressure of the piston rod on the piston.

2. A medication delivery device (1) according to claim 1, characterized in that the resilient member is arranged to move the drive member and thereby the piston rod in the proximal direction with respect to the housing after dose delivery such that the piston rod is moved away from the piston by a distance in the range of 0.1 to 2.0 mm.

3. A medication delivery device (1) according to claim 1, characterized in that the drive member is releasably coupled to the piston rod such that the piston rod follows movement of the drive member in the distal direction with respect to the housing for delivering the dose and does not follow movement of the drive member in the proximal direction with respect to the housing for setting the dose.

4. A medication delivery device (1) according to claim 1, characterized in that the drive member comprises a first rack and the piston rod is coupled to the first rack via a pinion, wherein the pinion is engaged with a second rack and the second rack is connected to the housing.

5. A medication delivery device according to claim 4, characterized in that the second rack is formed unitarily with the housing or is secured against rotational and/or axial movement with respect to the housing.

6. A medication delivery device according to claim 1, characterized in that the drive member comprises a first supporting element and the piston rod is coupled to the first supporting element via a lever, wherein the lever is engaged with a second supporting element and the second supporting element is connected to the housing.

7. A medication delivery device according to claim 6, characterized in that the second supporting element is formed unitarily with the housing or is secured against rotational and/or axial movement with respect to the housing.

8. A medication delivery device according to claim 1, characterized in that the resilient member is formed integrally with the housing or integrally with an insert of the housing.

9. A medication delivery device according to claim 1, characterized in that the resilient member is arranged to mechanically interact with the drive member at a distal end of the drive member.

10. A medication delivery device according to claim 1, characterized in that the resilient member and the drive member are arranged for a force in the distal direction to be exerted on the resilient member during dose delivery such that the resilient member is biased in such a way that after dose delivery and after removing the force in the distal direction, the biased resilient member moves the drive member in the proximal direction with respect to the housing.

11. A method for operating the medication delivery device according to any one of the preceding claims, wherein
after having set a dose of medication (M) by moving the drive member in the proximal direction and after having moved the drive member in the distal direction for delivering the dose by exerting a force acting on the drive member in the distal direction, wherein the force in the distal direction causes the piston rod to move in the distal direction with respect to the housing and the resilient member to be biased, the method comprises the steps of
waiting for a preset period of time, and thereafter
removing the force in the distal direction from the drive member with the drive member being moved in the proximal direction with respect to the housing by mechanical interaction of the biased resilient member and the drive member, which mechanical interaction causes movement of the piston rod in the proximal direction with respect to the housing.

12. A method according to claim 11, wherein the piston is elastically deformed during movement of the piston rod in the distal direction and wherein the piston starts to resume its undeformed shape by relaxing in the distal direction during the preset period thereby expelling medication (M) from the cartridge.

13. A method according to claim 12, wherein the piston continues to resume its undeformed shape by relaxing in the proximal direction after the piston rod has been moved in the proximal direction.

14. A method according to claim 13, wherein the preset period of time is greater than or equal to 5 seconds and less than or equal to 15 seconds.

15. A method according to claim 14, wherein a restriction member limits that movement of the drive member in the proximal direction with respect to the housing, which is caused by the resilient member.

16. A method according to claim 15, wherein the distance the drive member is moved in the proximal direction with respect to the housing after dose delivery caused by the resilient member is smaller than the distance the drive member is movable in the proximal direction for setting the dose of medication (M) to be delivered.

17. A method according to claim 13, wherein a restriction member limits that movement of the drive member in the proximal direction with respect to the housing, which is caused by the resilient member.

18. A method according to claim 13, wherein the distance the drive member is moved in the proximal direction with respect to the housing after dose delivery caused by the resilient member is smaller than the distance the drive member is movable in the proximal direction for setting the dose of medication (M) to be delivered.

19. A method according to claim 12, wherein the preset period of time is greater than or equal to 5 seconds and less than or equal to 15 seconds.

20. A method according to claim 12, wherein a restriction member limits that movement of the drive member in the proximal direction with respect to the housing, which is caused by the resilient member.

21. A method according to claim 12, wherein the distance the drive member is moved in the proximal direction with respect to the housing after dose delivery caused by the resilient member is smaller than the distance the drive member is movable in the proximal direction for setting the dose of medication (M) to be delivered.

22. A method according to claim 11, wherein the preset period of time is greater than or equal to 5 seconds and less than or equal to 15 seconds.

23. A method according to claim 11, wherein a restriction member limits that movement of the drive member in the proximal direction with respect to the housing, which is caused by the resilient member.

24. A method according to claim 11, wherein the distance the drive member is moved in the proximal direction with respect to the housing after dose delivery caused by the resilient member is smaller than the distance the drive member is movable in the proximal direction for setting the dose of medication (M) to be delivered.

* * * * *